United States Patent [19]

Bauer et al.

[11] 4,193,934

[45] Mar. 18, 1980

[54] NITRILES WITH ODORANT PROPERTIES

[75] Inventors: Kurt Bauer; Ulli Harder; Wolfgang Sturm, all of Holzminden, Fed. Rep. of Germany

[73] Assignee: Haarmann & Reimer GmbH, Holzminden, Fed. Rep. of Germany

[21] Appl. No.: 950,896

[22] Filed: Oct. 12, 1978

Related U.S. Application Data

[63] Continuation of Ser. No. 779,665, Mar. 21, 1977, abandoned, which is a continuation of Ser. No. 636,881, Dec. 2, 1975, abandoned, which is a continuation of Ser. No. 415,896, Nov. 14, 1973, abandoned.

[30] Foreign Application Priority Data

Nov. 17, 1972 [DE] Fed. Rep. of Germany ....... 2256483
Feb. 23, 1973 [DE] Fed. Rep. of Germany ....... 2308735
Sep. 26, 1973 [DE] Fed. Rep. of Germany ....... 2348359

[51] Int. Cl.² .................. C07C 121/68; C07C 121/70; C07C 121/46; C11B 9/00
[52] U.S. Cl. .................. 260/465 R; 260/464; 260/465 K; 252/522 R; 252/174; 252/174.11; 424/358; 424/69; 252/106
[58] Field of Search ........................ 260/465 R, 465 K; 252/522

[56] References Cited

U.S. PATENT DOCUMENTS

| | | | |
|---|---|---|---|
| 2,583,194 | 1/1952 | Weisler et al. | 260/464 X |
| 3,173,939 | 3/1965 | Johnson | 260/465.4 |
| 3,256,345 | 6/1966 | Solomon | 260/465 R |

OTHER PUBLICATIONS

Braun, et al., C.A., 6 (1912), pp. 2604–2605.
Ruzicka, et al., C.A., 26 (1932), pp. 4592–4593.
Mihina, et al., C.A., 45 (1951), pp. 2937–2938.
Pickard, et al., C.A., 46 (1952), pp. 441–442.
Honwad, et al., C.A., 63 (1965), p. 18172.
Cookson, et al., C.A., 64 (1966), p. 4898.
Wagner & Zook, Synthetic Organic Chemistry, (1953), p. 7.
Migrdichian, Organic Synthesis, vol. 2, (1957), pp. 899–900.
Bedoukian, "Perfumery and Flavoring Synthetics", (1967), pp. 99 and 112.
Arotander, "Perfume and Flavor Chemicals", (1969), items 649, 653 and 1451.

*Primary Examiner*—Joseph Paul Brust
*Attorney, Agent, or Firm*—Sprung, Felfe, Horn, Lynch & Kramer

[57] ABSTRACT

Compound of the formula

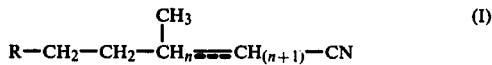
(I)

in which
n stands for 0 or 1 and, where "n" stands for 0, a double bond is present as indicated by the chain line, and
R represents a cyclohexyl radical, or a phenyl radical which may optionally be substituted in the p-position by a lower alkyl radical.

The compounds are produced by reaction of methylethyl ketone substituted in the β-position by R with cyanoacetic acid in the presence of a basic catalyst. The compounds are useful as perfumes.

9 Claims, No Drawings

NITRILES WITH ODORANT PROPERTIES

This is a continuation of Application Ser. No. 779,665, filed March 21, 1977, now abandoned, which is a continuation of Ser. No. 636,881, filed December 2, 1975, now abandoned which is a continuation of Ser. No. 415,896, filed November 14, 1973, now abandoned.

This invention relates to new nitriles, to a process for their production and to their use.

New compounds have been found which correspond to the general formula I

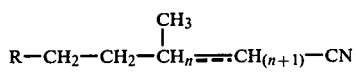

$$R-CH_2-CH_2-CH_n = CH_{(n+1)}-CN \qquad (I)$$

in which
  n represents 0 or 1 and, where "n" represents 0, a double bond is present in accordance with the chain line; and
  R represents a cyclohexyl radical or a phenyl radical which may optionally be substituted in the p-position by a lower alkyl radical.

Examples of lower alkyl radicals are branched or unbranched alkyl radicals having 1 to 5 carbon atoms. R preferably represents the cyclohexyl radical, the phenyl radical or the p-methyl-, p-ethyl-, p-n-propyl-, p-isopropyl- or p-tert.-butylphenyl radical and, with particular reference, the phenyl radical.

The compounds according to formula I can be present in the cis-form and in the trans-form where "n" represents 0.

The following are mentioned as examples of compounds which fall within the scope of general formula I: cis-5-phenyl-3-methyl-2-penten-1-oic acid nitrile, trans-5-phenyl-3-methyl-2-penten-1-oic acid nitrile, cis-5-(p-methylphenyl)-3-methyl-2-penten-1-oic acid nitrile, trans-5-(p-methylphenyl)-3-methyl-2-penten-1-oic acid nitrile, cis-5-(p-ethylphenyl)-3-methyl-2-penten-1-oic acid nitrile, trans-5-(p-ethylphenyl)-3-methyl-2-penten-1-oic acid nitrile, cis-5-(p-isopropylphenyl)-3-methyl-2-penten-1-oic acid nitrile, trans-5-(p-isopropylphenyl)-3-methyl-2-penten-1-oic acid nitrile, cis-5-p-n-propylphenyl)-3-methyl-2-penten-1-oic acid nitrile, trans-5-(p-n-propylphenyl)-3-methyl-2-penten-1-oic acid nitrile, 5-phenyl-3-methyl pentanoic acid nitrile, 5-(p-methylphenyl)-3-methyl pentanoic acid nitrile, 5-(p-ethylphenyl)-3-methyl pentanoic acid nitrile, 5-(p-isopropylphenyl)-3-methyl pentanoic acid nitrile, 5-(p-n-propylphenyl)-3-methyl pentanoic acid nitrile, 5-(p-tert.-butylphenyl)-3-methyl pentanoic acid nitrile, cis-5-cyclohexyl-3methyl-2-penten-1-oic acid nitrile, trans-5-cyclohexyl-3-methyl-2-penten-1-oic acid nitrile, 5-cyclohexyl-3-methyl-pentan-1-oic acid nitrile.

The invention also relates to a process for producing the nitriles of general formula I defined above which is characterised by the fact that substituted methylethyl ketones substituted in the β-position by a cyclohexyl-, phenyl-, p-methylphenyl-, p-ethylphenyl-, p-n-propylphenyl- or p-isopropylphenyl- or p-tert.-butylphenyl radical, are reacted with cyanoacetic acid in the presence of a basic, e.g. weakly basic, catalyst. This reaction produces a condensation product from which a product mixture, which contains the unsaturated formula I compounds according to the invention (n=0) which can be converted by hydrogenation into the saturated formula I compounds according to the invention (n=1), is formed in situ by decarboxylation under the aforementioned reaction conditions.

The following are mentioned as examples of substituted methylethyl ketones: β-cyclohexylmethylethyl ketone (=hexahydrobenzyl acetone), benzylacetone, p-methylbenzylacetone, p-ethylbenzylacetone, p-n-propylbenzylacetone, p-isopropylbenzylacetone and p-tert.-butylbenzylacetone.

Examples of weakly basic catalysts which are suitable for use in the process according to the invention include ammonia, ammonium salts, primary or secondary amines, pyridine, piperidine or quinoline, preferably ammonium acetate, pyridine and piperidine. The reaction which produces the condensation product in the process according to the invention is best carried out in an organic solvent. Preferred solvents are those which form azeotropic mixtures with water, for example benzene hydrocarbons, most preferably benzene, toluene and xylene.

Basically, the reaction temperature applied in the process according to the invention is not critical and, in general, can vary within the range from 20° to 180° C. The reaction is best carried out at temperatures in the boiling range of the particular solvent used. It is particularly advantageous, for example, to remove the water formed during the condensation reaction with the solvent by azeotropic distillation until the reaction is complete.

The reaction components cyanoacetic acid and the substituted methylethyl ketones are generally used in substantially equimolar quantities. In order to improve the yield, it is of course also possible to use the less expensive starting component in a slight excess.

The weakly basic catalyst used for the process according to the invention can be employed, for example, in quantities of from 0.01 to 2 mols, based on 1 mol of cyanoacetic acid.

After all the water formed during the reaction has been completely removed, the solvent and, optionally, the weakly basic catalyst as well are distilled off the unsaturated nitriles according to the invention can be obtained in pure form from the residue, for example by fractional vacuum distillation.

The reaction gives a product mixture which, in addition to the compounds according to the invention of general formula I, in which "n" stands for 0 also contains the compounds of general formulae II and III, in which R has the same scope of meaning as in formula I, formed through displacement of the double bond from the α,β-position into the β,γ- and β,γ'-position.

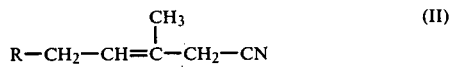

$$R-CH_2-CH=C-CH_2-CN \qquad (II)$$
     with CH₃ on the C

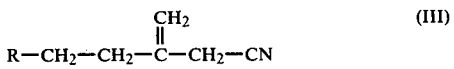

$$R-CH_2-CH_2-C-CH_2-CN \qquad (III)$$
     with =CH₂ on the C

Accordingly, mixtures obtained by the process according to the invention can consist of the 5-cyclohexyl derivatives and of the 5-phenyl derivatives, optionally substituted in the p-position, of cis- and trans-3-methyl-2-penten-1-oic acid nitrile, cis- and trans-3-methyl-3-penten-1-oic acid nitrile and 3-methylene pentanoic acid nitrile.

The required α,β-unsaturated compounds can be isolated from the product mixture by conventional preparative methods, for example by fractional distillation or by preparative gas chromatography.

The mixture of $\alpha,\beta$-, $\beta,\gamma$- and $\beta,\gamma'$-unsaturated compounds obtained by the process according to the invention, which generally contains from 10 to 50% by weight of the $\alpha,\beta$-isomers according to the invention, can be used as such for perfumery purposes or can be converted substantially quantitatively by isomerisation into the $\alpha,\beta$-unsaturated compounds.

In one preferred embodiment of the process according to the invention, the product mixture obtained from the reaction on which the process according to the invention is based can be isomerised with a base, preferably with a strong base, such as an alkali hydroxide or an alkali alcoholate for example, to form the corresponding $\alpha,\beta$-unsaturated compounds.

Alkali alcoholates are preferably used as bases for the isomerisation reaction, the following being mentioned by way of example: sodium methylate, sodium ethylate, sodium propylate and sodium butylate. It is particularly preferred to use sodium methylate.

Isomerisation is best carried out in a solvent which is inert to the reaction components. Examples of suitable solvents include the alcohols corresponding to the alcoholates used, such as methanol, ethanol, propanol and butanol; methanol being particularly preferred.

The base can be used for example in quantities of from 0.01 to 10 mols, based on 1 mol of the isomer mixture used, and is preferably used in quantities of from 0.1 to 1 mol.

The isomerisation reaction is carried out at a temperature of for example in the range from $-80°$ to $+120°$ C. and preferably at a temperature of from 0° to 50° C.

The reaction mixture is stirred or shaken under the aforementioned conditions until isomerisation is complete, which generally takes from 1 to 50 hours. It has proved to be particularly advantageous, for example, to keep to a reaction time of 1 to 5 hours in cases where 0.1 to 1 mol of base is used.

The corresponding $\alpha,\beta$-unsaturated compounds of formula I are obtained in this way from the product mixture used for isomerisation. The $\alpha,\beta$-unsaturated compounds generally accumulate in the form of mixtures of the particular cis-trans-isomers, the cis- and the trans-isomers being present for example in a ratio of cis- to trans- of from about 1:1 to about 1:3. A cis-trans-isomer mixture in a ratio of about 2:3 to 2:5, which as a mixture is particularly valuable for perfumery purposes is preferentially formed for example in cases where the base is used in a concentration of about 1 mol per mol of unsaturated compound in the reaction mixture for a reaction time of about 3 hours.

The cis-trans-isomer mixture which may be obtained by the process according to the invention can be used as such for perfumery purposes or can be separated by simple separation techniques into the cis- and trans-isomer.

Separation techniques which have proved to be advantageous include, for example, fractional distillation through packed columns or slotted-tube columns and prepreparative gas chromatography. By comparison with the cis-trans-isomer mixtures, the isolated cis- and trans-isomers create further possibilities for application in perfumery through differentiated fragrance notes.

Hydrogenation of the product mixture obtained by the process according to the invention into the compounds saturated in the 2,3-position is carried out selectively on the aliphatic double bond in the presence of a hydrogenation catalyst.

Hydrogenation catalysts which are used for the process according to the invention are catalysts which selectively hydrogenate the aliphatic double bond without affecting the nitrile group. Preferred hydrogenation catalysts are metals of the 8th Secondary Group of the Periodic System, for example palladium, platinum or their oxides, for example, platinum oxide. The catalysts are best applied to a supporting material. Particularly suitable supporting materials include, for example, carbon, kieselguhr, aluminum oxide, barium carbonate and calcium sulphate.

The hydrogenation catalyst can be used for example in quantities of from 0.0001 to 0.1 mol (based on the starting material), and is preferably used in quantities of from 0.001 to 0.01 mol.

The hydrogenation stage of the process according to the invention can be carried out for example with particularly good results at a temperature of from about 0° to 50° C. under an excess hydrogen pressure of from about 0 to 50 atms. Hydrogenation generally takes between about 0.5 and 5 hours, depending upon the particular hydrogenation conditions.

The saturated compound according to the invention of general formula I in which "n" represents 1 can be isolated from the reaction mixture after the catalyst has been filtered off and the solvent distilled off by fractional vacuum distillation as known per se.

The nitriles according to the invention are distinguished by particularly advantageous desirable odorant properties which can be characterised as radiant, intensive, persistant and harmonic. They represent valuable additions to the perfume materials hitherto available for the reproduction of citrus notes and fruit notes.

The use of conventional citrus odorants such as, for example, citral and citronellal, is attended by the disadvantage that these substances ae readily affected by aggressive media, especially acid media such as, for example, hair-care preparations or acid cleaning agents. Conventional citrus odorants that are unaffected by aggressive media, such as geranic acid nitrile for example, do not have satisfactory fragrance properties. For example, the aggressive nitrile note is very noticeable in the case of geranic acid nitrile, in addition to which persistance is inadequate.

By contrast, the compounds according to the invention exhibit outstanding odorant properties. Instead of the unpleasantly metallic nitrile note of geranic acid nitrile, the compounds according to the invention have a soft, warm citrus note. Their persistance is several times better than that of conventional citrus odorants. In compositions, it is possible to obtain a new fresh and long-lasting citrus note which is surprisingly stable in aggressive media. In addition, the nitriles according to the invention do not discolour when used in aggressive media.

The compounds according to the invention can be used as odorants per se either in pure form or in the form of isomer mixtures. They can also be employed in mixtures with other substances in odorant compositions, for example in quantities of from about 0.01 to 25% by weight and preferably in quantities of from about 0.1 to 10% by weight, based on the mixture as a whole.

The scope of application of the compounds according to the invention is unusually wide by virtue of their harmonic odour and their service properties such as, for example, their stability with respect to aggressive media. They are suitable for use in perfume compositions for numerous end products of the cosmetic, fine-perfumery, washing agent and commercial sectors, for example for detergents, washing powders, soaps, washing-up liquids, fabric conditioners, bath foams, shampoos, cleaning agents, hair-care preparations, hair dyes, cold perms, cold-perm setting agents, anti-perspirants, bath salts, deodorants, powders and creams.

EXAMPLE 1

1120 ml of toluene, 622 ml of pyridine, 21 g of ammonium acetate, 936 g (6.32 mol) of benzylacetone and 608 g (7 mol) of cyanoacetic acid (98%), were heated for 5 hours to boiling point in a 4-liter two-necked flask equipped with an internal thermometer and water separator with an intensive cooler. The solvent mixture was then distilled off.

The distillation residue was cooled to room temperature, followed by the addition of a solution of sodium methylate obtained by reacting 40 g (approximately 1.75 mol) of sodium in 1.75 l of methanol. The mixture was stirred for 3 hours at room temperature and then neutralised with 105 g (1.75 mol) of acetic acid, after which the solvent was distilled off while stirring. The distillation residue was poured onto 1 liter of ice water and the organic phase thus formed was separated off and subjected to fractional vacuum distillation. Distillation produced first runnings of about 120 g of benzylacetone and, at 94°–112° C./0.3 mm Hg, 856 g (5 mol corresponding to 79.1%, based on benzylacetone) of a mixture of cis- and trans-5-phenyl-3-methyl-2-penten-1-oic acid nitrile, the cis- and trans-isomers being present in a weight ratio of 2:3.

Refractive index: $n_D^{20} = 1.534$
Density: 0.97 at 25° C.
Odour, soft citrus-rose-like with aldehydic woody and musky nuances.

EXAMPLE 2

Following the procedure of Example 1, 1024 g (6.32 mol) of p-methylbenzylacetone, instead of 936 g (6.32 mol) of benzylacetone, were reacted with 7 mols of cyanoacetic acid. The reaction produced 870 g (4.7 mol) of a mixture of cis- and trans-5-(p-methylphenyl)-3-methyl-2-penten-1-oic acid nitrile, the cis- and trans-isomers being present in a weight ratio of 2:3.

Boiling point: 104°–112° C./0.5 mm Hg
Refractive index: $n_D^{20} = 1.530$
Density at 25° C: 0.97
Odour, green citrus-rose note with a fruity, woody nuance.

EXAMPLE 3

The procedure was as described in Example 1, except that 1110 g (6.32 mol) of p-ethylbenzylacetone instead of 936 g (6.32 mol) of benzylacetone were reacted with 7 mol of cyanoacetic acid. The reaction produced 916 g (4.6 mol) of a mixture of cis- and trans-5-(p-ethylphenyl)-3-methyl-2-penten-1-oic acid nitrile, the cis- and trans-isomers being present in a weight ratio of 2:3.

Boiling point: 107°–114° C./0.5 mm Hg
Refractive index: $n_D^{20} = 1.530$
Density at 25° C.; 0.97
Odour, green citrus note with a fruity and rose-like nuance.

EXAMPLE 4

The procedure was as described in Example 1, except that 1200 g (6.32 mol) of p-isopropylbenzylacetone instead of 936 g (6.32 mol) of benzylacetone were reacted with 7 mol of cyanoacetic acid. The reaction produced 1024 g (4.8 mol) of a mixture of cis- and trans-5-(p-isopropylphenyl)-3-methyl-2-penten-1-oic acid nitrile, the cis- and trans-isomers being present in a weight ratio of 2:3.

Boiling point: 110°–116° C./0.3 mm Hg
Refractive index: $n_D^{20} = 1.525$
Density at 25° C.: 0.95
Odour, sweet, citrus-yellow-plum-like, fruity with a very soft, fine wood note and rose nuance.

EXAMPLE 5

The procedure was as described in Example 1, except that 1200 g (6.32 mol) of p-n-propylbenzylacetone instead of 936 g (6.32 mol) of benzylacetone, were reacted with 7 mol of cyanoacetic acid. The reaction produced 960 g (4.5 mol) of a mixture of cis- and trans-5-(p-n-propylphenyl)-3-methyl-2-penten-1-oic acid nitrile, the cis- and trans-isomers being present in a weight ratio of 2:3.

Boiling point: 113°–120° C./0.3 mm Hg
Refractive index: $n_D^{20} = 1.524$
Density at 25° C.: 0.954
Odour: sweet, fruity, lemons, rose-like and woody nuance.

EXAMPLE 6

725 g of the mixture of cis- and trans-5-phenyl-3-methyl-2-penten-1-oic acid nitrile obtained in accordance with Example 1 were heated to boiling point in a 1 liter flask, and subjected to fractional distillation in a 1 meter packed column with an internal diameter of 3 cm which was filled with 350 g of Wilson spirals 2.0 mm in diameter and which was provided with a column head for adjusting the reflux ratio to 5:1. The fractions obtained between 88° and 89° C. and between 92° and 95° C. under a vacuum of 0.2 Torr were fractionated another twice through the same column. This gave 45 g of cis-5-phenyl-3-methyl-2-penten-1-oic acid nitrile with a constant boiling point of 82° C. at 0.15 Torr and 62 g of trans-5-phenyl-3-methyl-2-penten-1-oic acid nitrile with a constant boiling point of 94° C. at 0.2 Torr.

Refractive index:
cis-5-phenyl-3-methyl-2-penten-1-oic acid nitrile
$n_D^{20} = 1.531$
trans-5-phenyl-3-methyl-2-penten-1-oic acid nitrile
$n_D^{20} = 1.537$
Odour:
The odour properties of the cis- and trans-forms are different from one another. In addition to the citrus component of the cis-trans mixture, the cis-5-phenyl-3-methyl-2-penten-1-oic acid nitrile has a vague fruity acetamide-asparagus note.

The trans-5-phenyl-3-methyl-2-penten-1-oic acid nitrile has a very fine citrus note.

EXAMPLE 7

200 g of the mixture of cis- and trans-5-phenyl-3-methyl-2-penten-1-oic acid nitrile obtained in accordance with Example 1 were heated to boiling point in a 250 ml flask and distilled through an 80 cm long standardised slotted tube of the HMS 1000 type (manufactured by Messrs Fischer, Bonn-Bad Godesberg)

equipped with a column head to adjust the reflux ratio to 10:1. This produced about 40 g of cis-5-phenyl-3-methyl-2-penten-1-oic acid nitrile having a constant boiling point of 82° C. at 0.15 Torr, and about 60 g of trans-5-phenyl-3-methyl-2-penten-1-oic acid nitrile having a constant boiling point of 88° C. at 0.15 Torr.

The refractive index and odorant properties were indentical with the results reported in Example 6.

EXAMPLE 8

In a gas chromatograph (type GC 3 AH manufactured by Messrs. Shimadzu, Dusseldorf), 10 μl of the cis-trans-isomer mixtures obtained in Examples 2 to 5 were preparatively separated in 20 runs into the pure cis- and trans-isomers. Separation was carried out under the following conditions:
Column length: 3 m
Column diameter: 4 mm internal
Filling type OS 3, 14 manufactured by Perkin-Elmer (15 propyleneglycol in kieselguhr 60–100 mesh)
Carrier gas: helium
Carrier gas velocity: 52 ml/min
Temperature: 180° C.
Receiver coolant: liquid nitrogen.

The following quantities of cis- and trans-isomers were obtained in pure form:
(a) Separation of the mixture of cis- and trans-5-(p-methylphenyl)-3-methyl-2-penten-1-oic acid nitrile of Example 2: 70 mg of cis-5-(p-methylphenyl)-3-methyl-2-penten-1-oic acid nitrile (refractive index $n_D^{20}=1.527$) Odour: herb-like, rosy, citrus note, spicy clove note 90 mg of trans-5-(p-methylphenyl)-3-methyl-2-penten-1-oic acid nitrile (refractive index $n_D^{20}=1.532$) Odour: green citrus-like, geranium-like, spicy
(b) Separation of the mixture of cis- and trans-5-(p-ethylphenyl) 3-methyl-2-penten-1-oic acid nitrile of Example 3: 64 mg of cis-5-(p-ethylphenyl)-3-methyl-2-penten-b 1-oic acid nitrile (refractive index: $n_D^{20}=1.528$) Odour: herb-like, spicy, fruity, lemons 88 mg of trans-5-(p-ethylphenyl)-3-methyl-2-penten-1-oic acid nitrile (refractive index: $n_D^{20}=1.533$) Odour: citrus note, rosy, spicy
(c) Separation of the mixture of cis- and trans-5-(p-n-propylphenyl)-3-methyl-2-penten-1-oic acid nitrile of Example 5: 75 mg of cis-5-(p-n-propylphenyl)-3-methyl-2-penten-1-oic acid nitrile (refractive index: $n_D^{20}=1.522$) Odour: spicy, citrus note, fruity 92 mg of trans-5-(p-n-propylphenyl)-3-methyl-2-penten-1-oic acid nitrile (refractive index: $n_D^{20}=1.527$) Odour: fruity, citrus note, rosy, woody
(d) Separation of the mixture of the cis- and trans-5-(p-isopropylphenyl)-3-methyl-2-penten-1-oic acid nitrile of Example 4: 70 mg of cis-5-(p-isopropylphenyl)-3-methyl-2-penten-1-oic acid nitrile (refractive index: $n_D^{20}=1.524$) Odour: fruity, yellow plums, flowery-jasmine-like, citrus note 95 mg of trans-5-(p-isopropylphenyl)-3-methyl-2-penten-1-oic acid nitrile (refractive index: $n_D^{20}=1.527$) Odour: fruity, lemony, flowery, rosy, woody.

EXAMPLE 9

A mixture of 500 g (2.92 mols) of 5-phenyl-3-methyl-2-penten-1-oic acid nitrile (cis-trans-isomer mixture 2:3), which had been obtained in accordance with Example 1, 500 ml (396g) of methanol and 32 g of palladium catalyst (5% by weight of palladium on kieselguhr), was hydrogenated in a 2 liter autoclave at a temperature of around 20° C. under an excess hydrogen pressure of 20 atmospheres. The absorption of hydrogen lasted 2 hours. The catalyst was then filtered off and the solvent of the filtrate distilled off. The distillation residue was subjected to fractional vacuum distillation in a 30 cm long Vigreux column.

Yield: 498 g (2.88 mols; 98.6% of the theoretical yield, based on nitrile used)
Boiling point: 98°–100° C./0.35 mm Hg
Refractive index: $n_D^{20}=1.5085$
Density (25° C.): 0.957
Odour: very pleasantly fruity, lemons, a little apple, a little orange.

EXAMPLE 10

A mixture of 500 g (2.7 mols) of 5-(p-methylphenyl)-3-methyl-2-penten-1-oic acid nitrile (cis-trans-isomer mixture 2:3), which had been obtained in accordance with Example 2, 500 ml (396 g) of methanol and 32 g of palladium catalyst (5% by weight of palladium on kieselguhr), was hydrogenated in a 2 liter autoclave at a temperature of around 20° C. under an excess hydrogen pressure of 20 atmospheres. The absorption of hydrogen lasted 2 hours. The catalyst was then filtered off and the solvent of the filtrate distilled off. The distillation residue was subjected to fractional vacuum distillation in a 30 cm long Vigreux column.

Yield: 477 g (2.55 mols, 94.4% of the theoretical yield)
Boiling point: 101°–102° C./0.35 mm Hg
Refractive index: $n_D^{20}=1.5075$
Density (25° C.): 0.946
Odour: anise-like, greasy, fatty, flowery.

EXAMPLE 11

A mixture of 500 g (2.51 mols) of 5-(p-ethylphenyl)-3-methyl-2-penten-1-oic acid nitrile (cis-trans-isomer mixture 2:3), which had been obtained in accordance with Example 3, 500 ml (396 g) of methanol and 32 g of palladium catalyst (5% by weight of Pd on kieselguhr), was hydrogenated in a 2 liter autoclave at a temperature of around 20° C. under an excess hydrogen pressure of 20 atmospheres. The absorption of hydrogen lasted 2 hours. The catalyst was then filtered off and the solvent of the filtrate distilled off. The distillation residue was distilled in vacuo through a 30 cm long Vigreux column.

Yield: 483 g (2.4 mols, 95.6% of the theoretical yield)
Boiling point: 142°–145° C./1.7 mm Hg
Refractive index: $n_D^{20}=1.5061$
Density (25° C.): 0.941 Odour: mild, woody-flowery, jasmine-like, somewhat green.)

EXAMPLE 12

A mixture of 500 g (2.35 mols) of 5-(p-isopropylphenyl)-3-methyl-2-penten-1-oic acid nitrile (cis-trans-isomer mixture 2:3), which had been obtained in accordance with Example 4, 500 ml) 396 g) of methanol and 32 g of palladium catalyst (5% by weight of palladium on kieselguhr), was hydrogenated in a 2 liter autoclave at a temperature of around 20° C. under an excess hydrogen pressure of 20 atmospheres. The absorption of hydrogen lasted 2 hours. The catalyst was then filtered off and the solvent of the filtrate distilled off. The distillation residue was distilled in vacuo through a 30 cm long Vigreux column Yield: 486 g (2.26 mols; 96.2% of the theoretical yield)

Boiling point: 124°–128° C./0.4 mm Hg
Refractive index: $n_D^{20}=1.5038$
Density: (25° C.): 0.934
Odour: mild, sweet, flowery, woody, green.

EXAMPLE 13

A mixture of 500 g (2.35 mols) of 5-(p-n-propylphenyl)-3-methyl-2-penten-1-oic acid nitrile (cis-trans-isomer mixture 2:3), which had been obtained in accordance with Example 5, 500 ml (396 g) of methanol and 32 g of palladium catalyst (5% by weight of Pd on kieselguhr), was hydrogenated in a 2 liter autoclave at a temperature of around 20° C. under an excess hydrogen pressure of 20 atmospheres. The absorption of hydrogen lasted 2 hours. The catalyst was then filtered off and the solvent of the filtrate distilled off. The distillation residue was distilled in vacuo through a 30 cm long Vigreux column.

Yield: 471 g (2.19 mols; 93.2% of the theoretical)
Boiling point: 150°–152° C./2.4 mm Hg
Refractive index: $n_D^{20}=1.5035$
Density at 25° C.: 0.935
Odour: mild, woody-flowery, somewhat green.

EXAMPLE 14

The synthesis of a cis-trans-isomer mixture of 5-(p-tert.-butylphenyl)-3-methyl-2-penten-1-oic acid nitrile was carried out in accordance with Example 1 with p-tert.-butyl-benzylacetone instead of benzylacetone.

The resulting mixture of 500 g (2.2 mols) of 5-(p-tert.-butylphenyl)-3-methyl-2-penten-1-oic acid nitrile (cis-trans-isomer mixture 2:3), 500 ml (396 g) of methanol and 32 g of palladium catalyst (5% by weight of palladium on kieselguhr), was hydrogenated in a 2 liter autoclave at a temperature of around 20° C. under an excess hydrogen pressure of 20 atmospheres. The absorption of hydrogen lasted 2 hours. The catalyst was was then filtered off and the solvent of the filtrate distilled off. The distillation residue was distilled in vacuo through a 30 cm long Vigreux column.

Yield: 479 g (2.09 mols; 95% of the theoretical yield)
Boiling point: 122°–126° C.
Refractive index: $n_D^{20}=1.5032$
Density (25° C.): 0.929
Odour: mild, sweet, woody, flowery, green.

EXAMPLE 15

1120 ml of toluene, 622 ml of pyridine, 21 g of ammonium acetate, 973 g (6.32 mol) of hexahydrobenzyl acetone and 608 g (7 mols) of cyanoacetic acid (98%) were heated for 5 hours to boiling point in a 4 liter two-necked flask equipped with an internal thermometer and a water separator with an intensive cooler. The solvent mixture was then distilled off.

The distillation residue was cooled to room temperature, followed by the addition of a solution of sodium methylate which had been obtained by reacting 40 g (approximately 1.75 mol) of sodium in 1.75 l of methanol. The mixture was stirred for 3 hours at room temperature and then neutralised with 105 g (1.75 mol) of acetic acid, after which the solvent was distilled off while stirring. The distillation residue was poured on to 1 liter of ice water and the organic phase formed was separated off and subjected to fractional distillation in vacuo. Distillation gave first runnings of approximately 120 g of hexahydrobenzyl acetone and, at 103°–108° C./1 mm Hg, 885 g (5 mols, corresponding to 79.1% based on hexahydrobenzyl acetone) of a mixture of cis- and trans-5-cyclohexyl-3-methyl-2-penten-1-oic acid nitrile, the cis- and trans-isomers being present in a ratio by weight of 2:3.

Refractive index: $n_D^{20}=1.485$
Density at 25° C. 0.910
Odour: fruity, sweet-citrus like, with a branny metallic cinnamon nuance.

EXAMPLE 16

725 g of the mixture of cis- and trans-5-cyclohexyl-3-methyl-2-penten-1-oic acid nitrile obtained in accordance with Example 15 were heated to boiling point in a 1 liter flask and subjected to fractional distillation in a 1 meter packed column with an internal diameter of 3 cm which was filled with 350 g of Wilson spirals 2.0 mm in diameter and which was provided with a column head to adjust the reflux ratio to 5:1. The fractions obtained between 103° and 105° C. and between 106° and 108° C. under a vacuum of 1.1 Torr were fractionated another twice through the same column. This produced 30 g of cis-5-cyclohexyl-3-methyl-2-penten-1-oic acid nitrile with a constant boiling point of 103° C. at 1.1 Torr, and 41 g of trans-5-cyclohexyl-3-methyl-2-penten-1-oic acid nitrile with a constant boiling point of 108° C. at 1.1 Torr.

Refractive index:
cis-5-cyclohexyl-3-methyl-2-penten-1-oic acid nitrile $n_D^{20}=1.481$
trans-5-cyclohexyl-3-methyl-2-penten-1-oic acid nitrile $n_D^{20}=1.488$
Odour: The odorant properties of the cis- and trans-forms are different from one another. In addition to the cirtus component of the cis-trans mixture, the cis-5-cyclohexyl-3-methyl-2-penten-1-oic acid nitrile was a vague watery, fruity, asparagus note.

The trans-5-cyclohexyl-3-methyl-2-penten-1-oic acid nitrile has a soft aldehydic, citrus note.

EXAMPLE 17

A mixture of 500 g (2.82 mols) of 5-cyclohexyl-3-methyl-2-penten-1-oic acid nitrile (cis-trans isomer mixture 2:3), which had been obtained in accordance with Example 15, 500 ml (396 g) of methanol and 32 g of palladium catalyst (5% by weight of Pd on kieselguhr), was hydrogenated in a 2 liter autoclave at a temperature of around 20° C. under an excess hydrogen pressure of 20 atmospheres. The absorption of hydrogen lasted 2 hours. The catalyst was then filtered off and the solvent of the filtrate distilled off. The distillation residue was subjected to fractional distillation in vacuo in a 30 cm long Vigreux column.

Yield: 496 g (2.77 mols; 98.2% of the theoretical yield, based on nitrile used)
Boiling point: 80° C./0.15 mm Hg
Refractive index: $n_D^{20}=1.462$
Density at 25° C.: 0.889
Odour: Waxy and formate-like, light lemon note with fruity and cinnamon-like nuances.

EXAMPLE 18

(a) Perfume compositions prepared with the product mixture of Example 1 (Recipe I):

400 parts by weight of bergamot oil;
270 parts by weight of lemon oil;
130 parts by weight of orange oil (bitter);
70 parts by weight of petit-grain oil;
30 parts by weight of mandarin oil;

| |
|---|
| 17 parts by weight of muscatel sage oil; |
| 5 parts by weight of hydroxy citronellal; |
| 20 parts by weight of α-hexyl cinnamaldehyde; |
| 5 parts by weight of geranium oil; |
| 5 parts by weight of East Indian sandalwood oil; |
| 15 parts by weight of vetiveryl acetate; |
| 5 parts by weight of patchouli oil; |
| 3 parts by weight of ethyl citronellyl oxalate; and |
| 25 parts by weight of the product mixture of Example 1 |
| 1000 parts by weight |

By adding the product mixture of Example 1, this recipe is given a fresher, rounded-off note which could not be obtained without the addition of the mixture of Example 1. The fresh, rounded-off note remained in evidence up to the after-odour and persisted for an extremely long time in comparison with conventional citrus notes.

(b) Perfume composition prepared with the product mixture of Example 2.

25 Parts of the product mixture of Example 2 were worked into recipe I instead of 25 parts of the product mixture of Example 1. By comparison with the corresponding recipe without any of the compounds according to the invention, addition of the product mixture of Example 2 gave the initial odour a very fresh, natural lemon note which persisted into the after-odour.

(c) Perfume composition prepared with the product mixture of Example 3.

25 parts by weight of the product mixture of Example 3 were worked into recipe I instead of 25 parts of the mixture of Example 1. By comparison with the corresponding recipe without any of the compounds according to the invention, addition of the product mixture of Example 3 gave this recipe a fresh, citrus note which was still distinctly in evidence in the after-odour.

(d) Perfume composition prepared with the product mixture of Example 4.

25 parts of the product mixture of Example 4 were worked into recipe I instead of 25 parts of the product mixture of Example 1. By comparison with the corresponding recipe without any of the compounds according to the invention, addition of the product mixture of Example 4 produced a particularly long-lasting lemony, slightly organge-like note.

(e) Perfume composition prepared with the product mixture of Example 5.

25 parts of the product mixture of Example 5 were worked into recipe I instead of 25 parts of the product mixture of Example 1. In comparison with the corresponding recipe without any of the compounds according to the invention, the initial odour had a citrus-like lemony note which produced a pleasantly fresh effect, especially in the after-odour.

An eaude-Cologne perfumed with the perfume compositions according to Example 18(a) to (e) had the following composition:
4% by weight of perfume oil of recipe I according to Examples 18 (a) to (e).
96% by weight of 80% ethyl aclohol.

EXAMPLE 19

A perfume composition which is suitable for perfuming soap had the following composition:

| |
|---|
| 6 parts by weight of trimethyl undecylone aldehyde; |
| 240 parts by weight of α-hexyl cinnamaldehyde; |
| 36 parts by weight of styrenyl acetate; |
| 67 parts by weight of phenylethyl alcohol; |
| 36 parts by weight of tetrahydrogeranoil; |
| 25 parts by weight of amyl salicylate; |
| 25 parts by weight of ylang-ylang oil; |
| 191 parts by weight of p-tert.-butyl cyclohexyl acetate; |
| 12 parts by weight of clove oil; |
| 6 parts by weight of α-ionone; |
| 60 parts by weight of Morroccan cedar wood oil; |
| 50 parts by weight of vetiveryl acetate; |
| 36 parts by weight of patchouli oil; |
| 24 parts by weight of cinnamic alcohol; |
| 6 parts by weight of oak moss absolue; |
| 60 parts by weight of Benzoe Sumatra resin; |
| 36 parts by weight of galaxolide (1,3,4,6,7,8-hexahydro-4,6,6,7,8,8-hexamethyl cyclopenta-γ-2-benzopyran); |
| 48 parts by weight of coumarin; and |
| 36 parts by weight of mixture of Example 1 |
| 1000 parts by weight |

100 g of soap chips are mixed with 1 g of the perfume composition until a soap mass of substantially homogeneous composition is obtained. After homogenisation, the soap mass is compressed to form a cake of soap.

EXAMPLE 20

A perfume oil which is suitable for perfuming washing agents was prepared in accordance with recipe II below:

| |
|---|
| 45 parts by weight of trimethyl undecylene aldehyde (10% solution in diethylphthalate); |
| 418 parts by weight of phenylethyl alcohol; |
| 150 parts by weight of tetrahydrogeranoil; |
| 45 parts by weight of eugenol methyl ether; |
| 60 parts by weight of cinnamic alcohol (10% solution in diethylphthalate); |
| 12 parts by weight of hex-3-en-1-ol; |
| 30 parts by weight of tetrahydrolinalool; |
| 30 parts by weight of α-ionone; |
| 60 parts by weight of trichloromethylphenyl carbinylacetate; and |
| 150 parts by weight of mixture of Example 1 |
| 1000 parts by weight |

In this recipe, addition of the product mixture of Example 1 changes the pure rose bouquet of the corresponding recipe without this product mixture into a perfumistically interesting complex reminiscent of fresh flowers. At the same time, persistence is considerably improved.

A fabric conditioner consisting of

| |
|---|
| 6.7% by weight of dimethyl distearyl ammonium chloride (approximately 75% commercial-grade product). |
| 0.5% by weight of allyl alcohol polyglycol ether containing 12 mols of ethylene oxide; |
| 0.2% by weight of perfume oil of recipe II; and |
| 92.6% by weight of distilled water |
| 100.0% by weight | was prepared as follows:

⅔ of the water were heated to 70°–80° C. and the dimethyl distearyl ammonium chloride and allyl alcohol polyglycol ether dissolved therein with stirring. The rest of the water was then added and stirring continued until the mixture had cooled to 45° C. The perfume oil was then added and the mixture stirred until the perfume oil had been uniformly dispersed in it. In order to avoid creaming or skin formation, the product is left to cool to room temperature in a covered vessel.

EXAMPLE 21

A hair-treatment emulsion was prepared in accordance with the following recipe:

A mixture A and a mixture B were initially prepared from the following constituents (quantities in parts by weight):

Mixture A 0.20 of emulsifier, fatty alcohol polyglycol ether based on oleyl alcohol with about 10 mols of ethylene oxide;
0.80 of emulsifier, fatty alcohol polyglycol ether based on oleyl alcohol-cetyl alcohol with approximately 5 mols of ethylene oxide;
3.00 of cetyl alcohol;
0.50 of wool fat alcohol oxethylate with approximately 10 mols of ethylene oxide; and
20.00 of distilled water

Mixture B 71.80 of distilled water;
0.20 of sorbic acid;
0.50 of lauryl pyridinium chloride;
0.40 of citric acid;
5.00 of sorbitol (70% aqueous solution);
0.30 of polyvinyl pyrrolidone; and
0.30 of product mixture of Example 1

Preparation of Mixture A

All the constituents were mixed while stirring at 70° C.

Preparation of Mixture B

The sorbic acid was dissolved in the distilled water while stirring at 90° C. The solution is left to cool to 50° C. and the remaining constituents of the mixture added with stirring at that temperature.

Mixture B was added with stirring to Mixture A, Mixture A being adjusted to a temperature of 70° C. and Mixture B to a temperature of 55° C. before admixture. The mixture is left to cool to 40° C. with continued stirring and then homogenised.

EXAMPLE 22

1 g of the product mixture of Example 1 was worked into 100 g of soap mass so that substantially homogeneous composition was obtained. After homogenisation, the soap mass was comprised into a cake of soap. The resulting soap was distinguished by a fresh radiant citrus-rosy odour with a certain cosmetic note.

EXAMPLE 23

The procedure was as described in Example 22, except that, instead of 1 g of the product mixture of Example 1, 1 g of the product mixture of Example 2 was worked into a soap mass. The soap thus obtained was distinguished by a pleasantly lemony, fresh, slightly fruity-flowery odour.

EXAMPLE 24

The procedure was as in Example 22, except that instead of 1 g of the product mixture of Example 1 1 g of the product mixture of Example 3 was worked into a soap mass. The resulting soap was distinguished by a fruity, lemony, fresh odour.

EXAMPLE 25

The procedure was as in Example 22, except that instead of 1 g of the product mixture of Example 1 1 g of the product mixture of Example 4 was worked into a soap mass.

The resulting soap was distinguished by a weakly cirtrus odour.

EXAMPLE 26

The procedure was as described in Example 22, except that instead of 1 g of the product mixture of Example 1 1 g of the product mixture of Example 5 was worked into a soap mass.

The resulting soap was distinguished by a weakly fruity odour.

EXAMPLE 27

Perfume compositions based on the following recipe (recipe III, quantities in parts by weight):
403 of bergamot oil;
270 of lemon oil;
130 of orange oil (bitter);
70 of petit-grain oil;
30 of mandarin oil;
17 of muscatel sage oil;
5 of hydroxy citronellal;
20 of α-hexyl cinnamaldehyde;
5 of geranium oil;
5 of East Indian Sandalwood oil;
15 of vetiveryl acetate; and
5 g of patchouli oil (a) 25 parts by weight of the product of Example 9 were additionally worked into the recipe III. By comparison with recipe III without the product of Example 9 added, the composition had a very interesting, fresh lemony head note. The complex rounded off the note particularly well, and persisted for an extremely long time by comparison with conventional citrus notes.

(b) 25 parts by weight of the product of Example 10 were additionally worked into recipe III. By comparison with recipe III without the product of Example 10 added, the composition had a sweet, fruity-blossomy peak reminiscent of lilacs, jasmine, which persisted into the after odour. The orange note of the complex was intensified.

(c) 25 parts by weight of the product of Example 11 were additionally worked into recipe III. By comparison with recipe III without the product of Example 11 added, the composition had a fresh citrus note which was still distinctly in evidence in the after-odour.

(d) 25 parts by weight of the product of Example 12 were additionally worked into recipe III. By comparison with recipe without the product of Example 12 added, the composition had a pleasant creamy-perfumistic note.

(e) 25 parts by weight of the product of Example 13 were additionally worked into recipe III. By comparison with recipe III without the product of Example 13 added, the composition had a citrus, lemony note in its initial odour which produced a pleasantly fresh affect, especially in the after odour.

Eau-de-Colognes were prepared with the perfume compositions according to Example 27a to (e), consisting in each case of 4% by weight of the perfume compositions according to Example 27a. to (e) and of 96% by weight of ethyl alcohol (80%).

EXAMPLE 28

(a) A perfume composition which is suitble for perfuming soap had the following composition:

```
   6 parts by weight of trimethyl undecylene aldehyde;
 240 parts by weight of α-hexyl cinnamaldehyde;
  36 parts by weight of styrenyl acetate;
  67 parts by weight of phenylethyl alcohol;
  36 parts by weight of tetrahydrogeraniol;
  25 parts by weight of amyl salicylate;
 191 parts by weight of p-tert.-butyl cyclohexyl acetate;
  12 parts by weight of clove oil;
   6 parts by weight of α-ionone;
  60 parts by weight of Morroccan cedar wood oil;
  50 parts by weight of vetiveryl acetate;
  36 parts by weight of patchouli oil;
  24 parts by weight of cinnamic alcohol;
   6 parts by weight of oak moss absolue;
  60 parts by weight of Benzoe Sumatra resin;
  36 parts by weight of galaxolide (1,3,4,6,7,8-hexahydro-
     4,6,6,7,8,8-hexamethyl cyclopenta-
     γ-2-benzopyran);
  48 parts by weight of coumarin; and
  36 parts by weight of the product of Example 9
1000 parts by weight
```

Addition of the product of Example 9 gave the composition a stronger, refreshing lemon note by comparison with the corresponding composition without the product of Example 9 added.

(b) If the product of Example 9 in the composition according to Example 28a is replaced by the product of Example 10 the composition is given a flowery, anise-like note.

(c) If the product of Example 9 in the composition according to Example 28a is replaced by the product of Example 12, the composition is given a harmonic, rounded-off creamy wood note.

1000 g of soap chips were mixed with 1 g of each of the perfume compositions according to Example 28(a) to (c) until soap masses of substantially homogeneous composition were obtained. After homogenisation, the soap masses were compressed into a cake of soap.

EXAMPLE 29

A perfume oil which is suitable for perfuming washing agents has the following composition (recipe IV):

```
  45 parts by weight of trimethyl undecylene aldehyde
     (10% solution in diethylphthalate);
 418 parts by weight of phenylethyl alcohol;
 150 parts by weight of tetrahydrogeranoil;
  45 parts by weight of eugenol methyl ether;
  60 parts by weight of cinnamic alcohol (10% solution
     in diethylphthalate);
  12 parts by weight of hex-3-en-1-ol;
  30 parts by weight of tetrahydrolinalool;
  30 parts by weight of α-ionone;
  60 parts by weight of trichloromethylphenyl carbinyl
     acetate; and
 150 parts by weight of the product of Example 9
1000 parts by weight
```

By comparison with the corresponding recipe without the product of Example 9 added, the rose bouquet in recipe IV is given a fresh, lemony note. At the same time, persistance is considerably improved by the addition.

By adding the product of Example 10 instead of the product of Example 9, the pure rose bouquet in recipe IV is given a fruity note. At the same time, persistence is considerably improved by the addition.

By adding the product of Example 12 instead of the product of Example, the pure rose bouquet in recipe IV is given a very flowery note pleasantly reminiscent of rose blooms. At the same time, persistence is considerably improved by the addition.

A fabric conditioner consisting of

```
  8.7 parts by weight of dimethyl distearyl ammonium
      chloride (approximately 75%
      commercial-grade product);
  0.5 parts by weight of allyl alcohol polyglycol ether
      containing 12 mols of ethylene oxide;
  0.2 parts by weight of perfume oil of recipe IV; and
 92.6 parts by weight of distilled water.
100.0 parts by weight
``` was prepared as follows:

Two thirds of the water was heated to 70°–80° C. and the dimethyl distearyl ammonium chloride and allyl alcohol polyglycol ether were dissolved therein while stirring. The rest of the water may then added and stirring was continued until the mixture had cooled to 45° C. The perfume oil was then added and stirring was continued until the perfume oil had been uniformly dispersed. In order to avoid creaming or skin formation, the product was left to cool to room temperature in a covered vessel.

EXAMPLE 30

A hair-treatment emulsion was prepared in accordance with the following recipe:

A mixture A and a mixture B were initially prepared from the following constituents (quantities in parts by weight):

Mixture A 0.20 of emulsifier, fatty alcohol polyglycol ether based on oleyl alcohol-cetyl alcohol with approximately 10 mols of ethylene oxide;

0.80 of emulsifier, fatty alcohol polyglycol ether based on oleyl alcohol-cetyl alcohol with approximately 5 mols of ethylene oxide;

3.00 of cetyl alcohol;

0.50 of wool fat alcohol oxethylate with approximately 10 mols of ethylene oxide; and 20.00 of distilled water.

Mixture B 71.80 of distilled water;
0.20 of sorbic acid;
0.50 of lauryl pyridinium chloride;
0.40 of citric acid;
5.00 of sorbitol (70% aqueous solution);
0.30 of polyvinyl pyrrolidone; and
0.30 of the product of Example 9.

Preparation of Mixture A

All the constituents were mixed while stirring at 70° C. Preparation of Mixture B:

The sorbic acid was dissolved in the distilled water while stirring at 90° C. The solution was left to cool to 75° C. and the remaining constituents of the mixture were added with stirring at that temperature.

Mixture B was added with stirring to Mixture A, Mixture A having been adjusted to a temperature of 70° C. and Mixture B to a temperature of 55° C. before admixture. The mixture was allowed to cool to 40° C. with continued stirring and was then homogenised.

EXAMPLE 31

100 g of soap chips were mixed with 1 g of the product of Example 9 until a soap mass of substantially homogeneous composition was obtained. After homogenisation, the soap mass was compressed into a cake of soap.

The resulting soap was distinguished by a fresh, lemony fragrance which smelt very pleasant on the skin and persisted well.

EXAMPLE 32

The procedure was as in Example 31, except that instead of 1 g of the product of Example 9 1 g of the product of Example 10 was worked into a soap mass. The soap thus obtained was distinguished by an anise-hawthorn-like note.

EXAMPLE 33

The procedure was as in Example 31, except that instead of 1 g of the product of Example 9 1 g of the roduct of Example 11 was worked into a soap mass.

The reslting soap was distinguished by a fruity, lemony fresh odour.

EXAMPLE 34

The procedure was as in Example 31, except that instead of 1 g of the product of Example 9 1 g of the product of Example 12 was worked into a soap mass.

The resulting soap was distinguished by a fresh, cosmetic, lemony-woody note.

EXAMPLE 35

The procedure was as in Example 31, except that instead of 1 g of the product of Example 9 1 g of the product of Example 13 was worked into a soap mass. The soap thus obtained was distinguished by a weak fruity odour.

EXAMPLE 36

(a) Perfume composition prepared with the product mixture of Example 15(recipe V):

| | |
|---|---|
| 400 | parts by weight of bergamot oil; |
| 270 | parts by weight of lemon oil; |
| 130 | parts by weight of organge oil (bitter); |
| 70 | parts by weight of petit-grain oil; |
| 330 | parts by weight of mandarin oil; |
| 17 | parts by weight of muscatel sage oil; |
| 5 | parts by weight of hydroxycitronellal; |
| 20 | parts by weight of α-hexylcinnamaldehyde; |
| 5 | parts by weight of geranium oil; |
| 5 | parts by weight of East Indian sandalwood oil; |
| 15 | parts by weight of vetiveryl acetate; |
| 5 | parts by weight of pachouli oil; |
| 3 | parts by weight of ethyl citronellyl oxalate; and |
| 25 | parts by weight of the product mixture of Example 15 |
| 1000 | parts by weight |

Addition of the product mixture of Example 15 gave this recipe a fresher, rounded off note which could not be achieved without adding the mixture of Example 15. The fresh, rounded-off note remained in evidence in the after-odour and persisted for an extremely long time in comparison with conventional citrus notes.

(b) Instead of 25 parts of the product mixture of Example 15,25 parts of the product of Example 17 were worked into recipe V. By comparison with the corresponding recipe without the compound according to the invention added, the composition was given an interesting, fresh lemony head note by the product of Example 17. The composition had a very good rounding-off effect. The lemony note persisted for an extremely long time in comparison with conventional citrus notes.

Perfume compositions with the cau-de-Cologne perfumed in accordance with Example 36a and 36b can be made up as follows:

4% by weight of perfume oil with the recipe according to

Example 36a and 36b; and

96% by weight of 80% ethyl alcohol

EXAMPLE 37

A perfume composition which is suitable for perfuming soap had the following composition:

| | |
|---|---|
| 6 | parts by weight of trimethyl undecyclene aldehyde; |
| 240 | parts by weight of α-hexyl cinnamaldehyde; |
| 36 | parts by weight of styrenyl acetate; |
| 67 | parts by weight of phenylethyl alcohol; |
| 36 | parts by weight of tetrahydrogeranoil; |
| 25 | parts by weight of amyl salicylate; |
| 25 | parts by weight of ylang-ylang oil; |
| 191 | parts by weight of p-tert.-butyl cyclohexyl acetate; |
| 12 | parts by weight of clove oil; |
| 6 | parts by weigh of α-ionone; |
| 60 | parts weight weight of Morroccan cedarwood oil; |
| 50 | parts by weight of vetiveryl acetate; |
| 36 | parts by weight of patchouli oil; |
| 24 | parts by weight of cinnamic alcohol; |
| 6 | parts by weight of oak moss absolue; |
| 60 | parts by weight of Benzoe Sumatra resin; |
| 36 | parts by weight of galaxolide (1,3,4,6,7,8-hexahydro-4,6,6,7,8,8-hexamethyl cyclopenta-γ-2-benzopyran); |
| 48 | parts by weight of coumarin; and |
| 36 | parts by weight of the mixture of Example 15 |
| 1000 | parts by weight |

100 g of soap chips were mixed with 1 g of the perfume composition until a soap mass of substantially homogeneous composition was obtained. After homogenisation, the soap mass was compressed to form a cake of soap.

EXAMPLE 38

A perfume oil which was suitable for perfuming washing agents was made up in accordance with recipe VI below:

| | |
|---|---|
| 45 | parts by weight of trimethyl undecylene aldehyde, 10% solution in diethylphthalate; |
| 418 | parts by weight of phenylethyl alcohol; |
| 150 | parts by weight of tetrahydrogeranoil; |
| 45 | parts by weight of eugenolmethyl ether; |
| 60 | parts by weight of cinnamic alcohol, 10% solution in diethylphthalate; |
| 12 | parts by weight of hex-3-en-1-ol; |
| 30 | parts by weight of tetrahydrolinalool; |
| 30 | parts by weight of α-ionone; |
| 60 | parts by weight of trichloromethyl phenyl carbinyl acetate; and |
| 150 | parts by weight of the mixture of Example 15 |
| 1000 | parts by weight |

In this recipe, addition of the product mixture of Example 1 changed the pure rose bouquet of the corresponding recipe without this product mixture added into a perfumistically interesting complex reminiscent of fresh flowers. At the same time, persistence was considerably improved.

A fabric conditioner consisting of

| | |
|---|---|
| 6.7% | by weight of dimethyl distearyl ammonium chloride (approximately 75% commercial-grade product); |
| 0.5% | by weight of allyl alcohol polyglycol ether containing 12 mols of ethylene oxide; |
| 0.2% | by weight of perfume oil of recipe VI; |
| 92.6% | by weight of distilled water |
| 100.0% | by weight | was prepared as follows:

Two thirds of the water was heated to 70°–80° C., and the dimethyl distearyl ammonium chloride and allyl alcohol polyglycol ether were dissolved therein while stirring. The rest of the water was then added, and stirring was continued until the mixture had cooled to 45° C. The perfume oil was then added and stirring was continued until the perfume oil had been uniformly dispersed. In order to prevent creaming or skin formation, the product was left to cool to room temperature in a covered vessel.

EXAMPLE 39

A hair-treatment emulsion was prepared in accordance with the following recipe:

A mixture A and a mixture B were initially prepared from the following constituents (quantities in parts by weight):

Mixture A 0.20 of emulsifer, fatty alcohol polyglycol ether based on oleyl alcohol with approximately 10 mols of ethylene oxide;
0.80 of emulsifier, fatty alcohol polyglycol ether based on oleyl alcohol-cetyl alcohol with approximately 5 mols of ethylene oxide;
3.00 of cetyl alcohol;
0.50 of wool fat alcohol oxethylate with approximately 10 mols of ethylene oxide;
20.00 of distilled water;

Mixture B 71.80 of distilled water;
0.20 of sorbic acid;
0.50 of lauryl pyridinium chloride;
0.40 of citric acid;
5.00 of sorbitol (70% aqueous solution);
0.30 of polyvinyl pyrrolidone; and
0.30 of the product mixture of Example 15

Preparation of Mixture A

All the constituents were mixed while stirring at 70° C. Preparation of Mixture B:

The sorbic acid was dissolved in the distilled water while stirring at a temperature of 90° C. The solution was left to cool to 50° C. and the remaining constituents of the mixture were added with stirring at that temperature.

Mixture B was added with stirring to Mixture A, Mixture A having been adjusted to a temperature of 70° C. and Mixture B to a temperature of 55° C. before admixture. The mixture was left to cool to 40° C. with continued stirring, and then homogenised.

EXAMPLE 40

100 g of soap chips were mixed with 1 g of the product mixture of Example 15 until a soap mass of substantially homogeneous composition was obtained. After homogenisation, the soap mass was compressed into a cake of soap.

The resulting soap was distinguished by a fresh radiant citrus-like odour.

EXAMPLE 41

The procedure was as described in Example 40, except that instead of 1 g of the product mixture of Example 15 1 g of the product of Example 17 was worked into a soap mass.

The soap thus obtained was distinguished by a lemony, fresh and somewhat fruity-cinnamon-like odour.

What is claimed is:

1. Compound of the formula

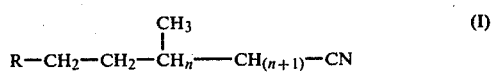

in which
n stands for 0 or 1 and, where n stands for 0, a double bond is present as indicated by the chain line and,
R represents phenyl which may optionally be substituted in the p-position by alkyl of 1–5 carbon atoms.

2. Compound according to claim 1, wherein n is 0.
3. Compound according to claim 1, wherein n is 1.
4. Compound as claimed in claim 1, wherein R is phenyl, p-methylphenyl, p-ethylphenyl, p-n-propylphenyl, p-isopropylphenyl, or p-tert.-butylphenyl.
5. Compound according to claim 2, wherein R is substituted in the p-position by an alkyl of 1–5 carbon atoms.
6. Compound according to claim 3, wherein R is substituted in the p-position by an alkyl of 1–5 carbon atoms.
7. Compound according to claim 1, which is cis- and trans-5-phenyl-3-methyl-2-penten-1-oic acid nitrile.
8. Compound according to claim 1, which is cis-5-phenyl-3-methyl-2-penten-1-oic acid nitrile.
9. Compound according to claim 1, which is trans-5-phenyl-3-methyl-2-penten-1-oic acid nitrile.

* * * * *